United States Patent [19]

Neurath et al.

[11] Patent Number: 4,495,296

[45] Date of Patent: Jan. 22, 1985

[54] LABELED ANTI-HAPTEN ANTIBODIES AND THEIR USE AS A UNIVERSAL REAGENT FOR SOLID PHASE RADIO- AND/OR ENZYME-IMMUNOASSAYS

[75] Inventors: A. Robert Neurath, New York; Nathan Strick, Far Rockaway, both of N.Y.

[73] Assignee: New York Blood Center, Inc., New York, N.Y.

[21] Appl. No.: 41,127

[22] Filed: May 21, 1979

[51] Int. Cl.[3] .................... G01N 33/52; G01N 33/54; G01N 33/56

[52] U.S. Cl. .................... 436/530; 436/543; 436/544; 436/545; 436/547; 436/804; 436/822; 435/4; 435/7

[58] Field of Search ............ 424/1, 12; 23/230 B; 435/4, 7

[56] References Cited

U.S. PATENT DOCUMENTS 4,185,084  1/1980  Mochida et al. ............ 424/1
4,230,683  10/1980  Decker et al. ............ 424/1

*Primary Examiner*—Christine M. Nucker

*Attorney, Agent, or Firm*—Sprung, Horn, Kramer & Woods

[57] ABSTRACT

A process for detecting the presence of an antigen in a specimen is described, which process comprises:

(A) contacting said specimen with a substrate coated with antibodies of said antigen, incubating the contacted substrate and washing the substrate;

(B) contacting the washed material of step (A) with a hapten conjugated antibody against said antigen, incubating the so-contacted material and washing the so-incubated material;

(C) contacting the washed material of step (B) with a radioactive material labeled or enzyme containing anti-hapten antibody, incubating the so-contacted material and washing the same; and (D) effecting radioimmunoassay if said antibody is radioactive or enzyme labeled immunoassay if said antibody contains an enzyme moiety.

Quantitative determination of the antigen in the specimen is effected by comparing the counts of the radioimmunoassay or the concentration of enzyme against a standard as by photocolormetric methods.

3 Claims, 3 Drawing Figures

LABELED ANTI-HAPTEN ANTIBODIES AND THEIR USE AS A UNIVERSAL REAGENT FOR SOLID PHASE RADIO- AND/OR ENZYME-IMMUNOASSAYS

ACKNOWLEDGMENT OF H.E.W. SUPPORT

The invention described herein was made in the course of or under grant HL 09011-15 from the National Institute of Health, Department of Health, Education and Welfare.

BACKGROUND OF THE INVENTION

1. Field of the Invention

This invention relates to a process for detecting the presence of an antigen in a specimen. More especially, this invention relates to the use of a universal labeled or enzyme containing antibody useful in the detection of a wide variety of antigens in a test specimen. More especially, this invention relates to the use of radioactive labeled or enzyme containing anti-hapten antibodies in the detection of the presence of and the amount of antigens in a test specimen.

2. Discussion of the Prior Art

Radioimmunoassay techniques for biochemical and immunological studies and for clinical research and diagnosis have become an invaluable tool. However, their applicability has been confined to reasonably well characterized antigens which can be purified and used for the preparation of antisera serving as a source for isolation of immunochemically purified antibodies. Although $^{125}I$-labeled staphylococcal protein A has been suggested as a general radioactive reagent for radioimmunoassay, it cannot be used for sandwich type tests with an antibody-coated solid phase. If neither antigen nor the corresponding antibody are available in relatively purified form, it becomes difficult to prepare radiolabeled reagents for radioimmunoassay (RIA) suitable for the detection of nanogram quantities of antigens.

It therefore became desirable to provide an process for the detection of and the quantitative measurement of antigens, which process could be used for those antibodies and antigens whose purification into relatively purified form was not heretofore known. More especially, it became desirable to provide a process by which nanogram quantities of antigens could be detected, which process did not rely upon the purification of antibodies and antigens as source material for the test. Still more especially, it became desirable to provide a process by which one could use a universal reagent for the detection of the presence of a wide variety of different types of antigens.

These and other objects of this invention will become more apparent from the ensuing description and claims.

SUMMARY OF THE INVENTION

In accordance with this invention, there is provided a process by which the presence of a wide variety of different types of antigen can be detected in test specimens. The process comprises:

(A) contacting a test specimen suspected of containing a given antigen with a substrate coated with antibodies of said antigen, incubating the contacted substrate and washing the substrate;

(B) contacting the washed material of step (A) with a hapten conjugated antibody against said antigen, incubating the so-contacted material and washing the so-incubated material;

(C) contacting the washed material of step (B) with a radioactive material labeled or enzyme containing anti-hapten antibody, incubating the so-contacted material and washing the same; and (D) effecting radioimmunoassay if said antibody is radioactive or enzyme labeled immunoassay if said antibody contains an enzyme moiety.

By conducting the process thusly, the quantitative presence of antigen can be determined without employing a purified source of antigen to prepare purified antibody. Qualitative determination of the antigen content in the specimen is effected by comparing the counts derived from the radioimmunoassay or the enzyme concentration in the case of enzyme labeled immunoassay (ELISA) with a standard known to be free of the antigen. Quantitative determination is effected by comparing the counts or enzyme concentration against data derived from the same test protocol using samples of known antigen concentrations.

The procedure of the invention takes advantage of the ability of anti-hapten antibody to readily react with hapten groups on the antibody employed in step (B) which has, in turn, reacted with antigen present in the test specimen. This antigen present in the test specimen has previously reacted with the corresponding antibody held on the substrate. By this technique, the initial antibody employed on the substrate need not be particularly pure and the quantity of antigen in the specimen is readily detected owing to magnification of test results as a result of the described sandwich technique wherein hapten conjugated groups on the antibody are reacted with anti-hapten antibody.

In accordance with the process, the substrate containing the antibody is contacted with test specimen containing the suspected antigen. The suspected antigen reacts with the antibody on the substrate and, in turn, is available for further reaction with a hapten conjugated antibody. When, in accordance with step (B), the hapten conjugated antibody contacts the antibody-antigen product resulting from step (A), there is formed a sandwich structure wherein the antigen is sandwiched on one side by the substrate-antibody reagent and on the other side by the hapten conjugated antibody.

The sandwich structure which results has available hapten groups, since it is the antibody portion of the hapten conjugated antibody that reacts with the antigen held by the substrate-antibody material used in step (A). This makes the hapten groups on the hapten conjugated antibody readily available for reaction with radio- or enzyme-labeled anti-hapten antibody. Since the hapten conjugated antibody can contain a multitude of hapten moieties, subsequent reaction with the labeled anti-hapten antibodies provides a substance which provides a magnified count whether analysis be by radioimmunoassay or ELISA. In other words, since the quantity of hapten moieties on the hapten conjugated antibody is many multiples of the number of antigens absorbed, a greater number of anti-hapten antibodies will react with those sites. This means that the number of counts per antigen is greater than in the standard radioimmunoassay techniques. This magnification permits the measurement of nanogram quantities of antigen in the test specimen. It is this magnification by the use of hapten conjugated antibody with the universal labeled anti-hapten antibody that permits use of antibody reagents in step (A) which are not particularly pure.

The process of the invention can be used with respect to any antigen, the presence of which is suspected in a given serum. All that is required is that an antibody of such suspected antigen be deposited on a substrate, that the specimen containing the suspected antigen contact the antibody on the substrate, incubation is effected and the so-incubated material is washed. Thereafter, in accordance with the second procedural series of steps, the washed material is contacted with hapten conjugated antibody against said antigen, which contacting is also followed by incubation and washing. These steps provide the hapten moieties on the antibody against the suspected antigen, which hapten moieties will react with radioactive labeled or enzyme containing anti-hapten antibody. Thereafter, the anti-hapten antibody which is either radioactive labeled or contains an enzyme is contacted with the washed material which is followed by incubation and washing. Radioimmunoassay or enzyme labeled immunoassay is effected to determine qualitatively the presence of the antigen and quantitatively the amount of antigen by comparison with pre-prepared standards. The higher the counts from a γ-counter or the higher concentration of enzyme in an ELISA test, the higher is the quantity of antigen in a test specimen.

Antigens whose presence and amount can be detected in accordance with the claimed process include essentially any antigen, for example viral, e.g., hepatitis B, influenza, adenovirus, and all other viral antigens, as well as bacterial antigens, tumor-specific antigens, serum antigens, enzyme proteins and all other antigens having at least two antigenic sites.

The antibodies of these antigens can be hapten conjugated with a wide variety of haptens including those which provide the following hapten moieties: dinitrophenyl, trinitrophenyl, diazotized sulfanilic acid, p-azobenzene arsonate, benzyl penicillin, p-azobenzoate, aspirin, fluorescein, isothiocyanate, p-iodobenzoate, p-(p'-hydroxyphenylazo) benzoate, phosphorylcholine and others.

The conjugation of haptens with proteins and the preparation of anti-hapten antibodies and their properties have been extensively reviewed (see, for example: "Advanced Immunochemistry", E. D. Day, Williams E. Williams, Baltimore, 1972; A. L. deWeck, "Low Molecular Weight Antigens" in: THE ANTIGENS, Ed. M. Sela, Academic Press, New York, 1974, Volume 2, pages 142–249).

Anti-hapten antibodies can be formed which correspond, in respect of the hapten moiety, to the hapten moiety on the conjugated antibody. Thus, the labeled anti-hapten antibody used in step (C) corresponds with respect to its hapten moiety to the hapten moiety of the hapten conjugated antibody against the suspected antigen. The same can be prepared in known manner, as by haptenating an antigen and introducing the so-haptenated antigen into a test animal, such as a rabbit, to effect an antibody response. As a result thereof, as is known, there is formed the antibody of the antigen and an anti-hapten antibody. The resultant serum is recovered and the anti-hapten antibody is separated from the other serum proteins including the antibody of the original antigen.

The anti-hapten antibody is thereafter labeled, either with a radioactive material such as $I^{125}$ or $I^{131}$ or is conjugated with an enzyme whereby there is formed an enzyme-containing anti-hapten antibody. This enzyme-containing anti-hapten antibody can then be used as a "labeled" anti-hapten antibody—labeled in the sense that it contains an enzyme, but is not radioactive. Detection of the absorption of the "labeled" anti-hapten antibody can be by RIA or ELISA in accordance with known techniques. RIA involves the use of a radiation detection means, whereas ELISA involves a measurement of the concentration of enzyme. The higher the enzyme concentration, the higher is the concentration of antigen adsorbed and the concentration of antigen in the original test specimen.

The incubation required in accordance with steps (A), (B), and (C) can be effected in known manner, such as under the following conditions: 1–8 hours at 37°–50° C. or 16–72 hours at 18°–30° C.

Washing is typically effected using an aqueous solution such as one buffered at a pH of 6–8, preferably at a pH of about 7, employing an isotonic saline solution.

BRIEF DESCRIPTION OF DRAWINGS

Referring to the drawings herein

Figure 1:
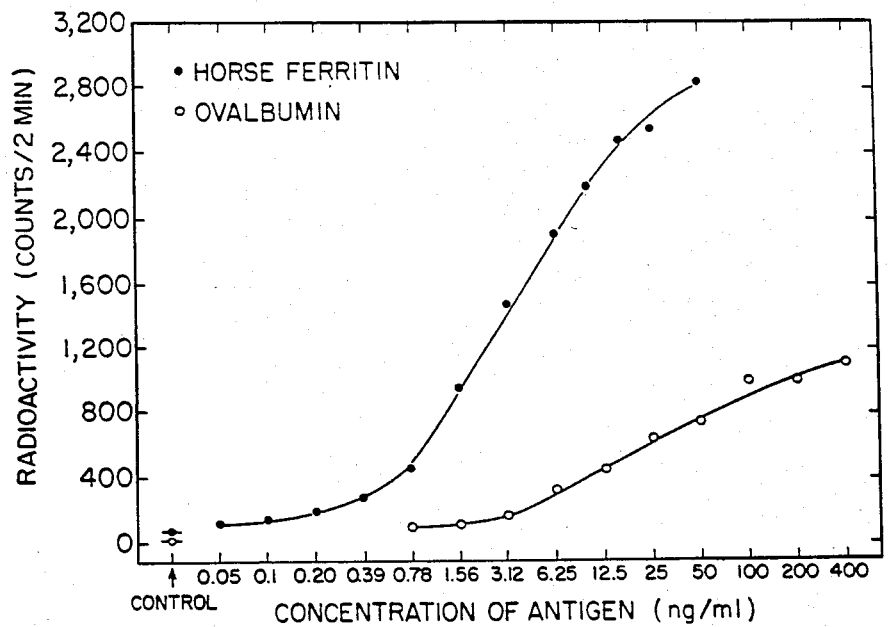
FIG. 1 shows the results of radioimmunoassay tests for ferritin and ovalbumin using a dinitrophenylated antibody. Normal human and sheep serum were used as diluent for ferritin and ovalbumin.

In order to more fully illustrate the nature of the invention and the manner of practicing the same, the following examples are presented:

EXAMPLES

Horse spleen ferritin and apoferritin were obtained from Sigma, St. Louis, Mo.; ovalbumin (5× crystallized), rabbit anti-ferritin and rabbit anti-DNP-bovine serum albumin (BSA) were obtained from Miles Laboratories, Elkhart, Ind.; goat anti-ovalbumin was from Research Products International Corp., Elk Grove Village, Ill. Tissue culture medium containing adenovirus group-specific complement-fixing (CF) antigen and the corresponding goat antiserum (CF titer 1:128) were obtained from Microbiological Associates, Walkersville, Md.

IgG isolated from the antisera by chromatography on DEAE-cellulose (H. H. Fudenberg, *Methods in Immunology and Immunochemistry*, Academic Press, New York, Volume 1, pages 321–324, 1967) was used to coat polystyrene beads (diameter 6 mm; Precision Plastic Ball Co., Chicago, Ill.) at a concentration of 100 μg/ml in 0.1 M tris-(hydroxymethyl) aminomethane, pH 8.8 (Neurath et al, *J. Gen. Virol.*, 38, 549–559, 1978). Aliquots of IgG (50 to 100 μg in 200 μl), dialyzed against 0.05 M borate pH 8.5 were labeled with 0.5 to 1.0 mCi of $^{125}$I-Bolton-Hunter reagent (Amersham, Arlington Heights, Ill.) overnight at 0° C. After addition of 200 μl of 1.0 M glycine-0.1 M borate pH 8.5 for 30 minutes, the labeled IgG was separated from other radioactive products by gel filtration on 0.7×20 cm columns of Sephadex G-75 using as eluant 0.05 M phosphate pH 7.5 containing 2.5 mg/ml of gelatine.

Dinitrophenylation of proteins was carried out as described (A. W. Wheeler and P. M. Hatcher, *J. Immunol. Methods*, 13, 29–37, 1976) except that the final concentration of sodium 2,4-dinitrophenylsulfonate was $10^{-2}$ and the pH was 9.5.

To isolate anti-DNP from anti-DNP-BSA, 2 ml of the antiserum were mixed with 10 mg of DNP-apoferrin. The mixture was incubated 1 hour at 37° C., overnight at 4° C., and centrifuged for 1 hour at 90,000 x g. The pellet was dissolved in 1 ml of 8 M urea-0.01 M phosphate pH 8.0–0.1 percent Nonidet P40 (BDH Chemicals, Ltd., Poole, England) (UPN) and applied to a 2 ml column of DEAE-cellulose (DE 52; Whatman, Springfield Mill, Maidstone, Kent, England) prewashed with UPN. Anti-DNP IgG recovered in the void volume of the column after elution with UPN was dialyzed first against 0.01 M tris (hydroxymethyl) aminomethane-0.14 M NaCl-0.02 percent $NaN_3$ (TS) containing 1 mg/ml of Nonidet P40 and then against 0.05 M borate pH 8.5 for labeling with $^{125}$I-Bolton-Hunter reagent.

For RIA tests, antibody coated beads were incubated overnight at 20° C. with dilutions of the corresponding antigens in normal sera (400 μl). The beads were washed with TS and then incubated with dinitrophenylated immunoglobulins (0.6 to 2.5 μg IgG per test), diluted in the same normal sera used for the first incubation (except in assays for HBeAg, for which normal human serum diluted 10-fold in fetal calf serum was used) for 2 hours at 37° C. The beads were washed with TS, incubated for 2 hours at 37° C. with $^{125}$I-anti-DNP (0.1 μCi per test; specific activity 1.2 μCi/μg) in the proper normal sera as before, washed with TS and counted in a γ-counter. In the direct RIA for HBeAg, beads were incubated with $^{125}$I-Bolton-Hunter reagent labeled antibodies to HBeAg (anti-HBe) instead of dinitrophenylated anti-HBe.

Figure 2:
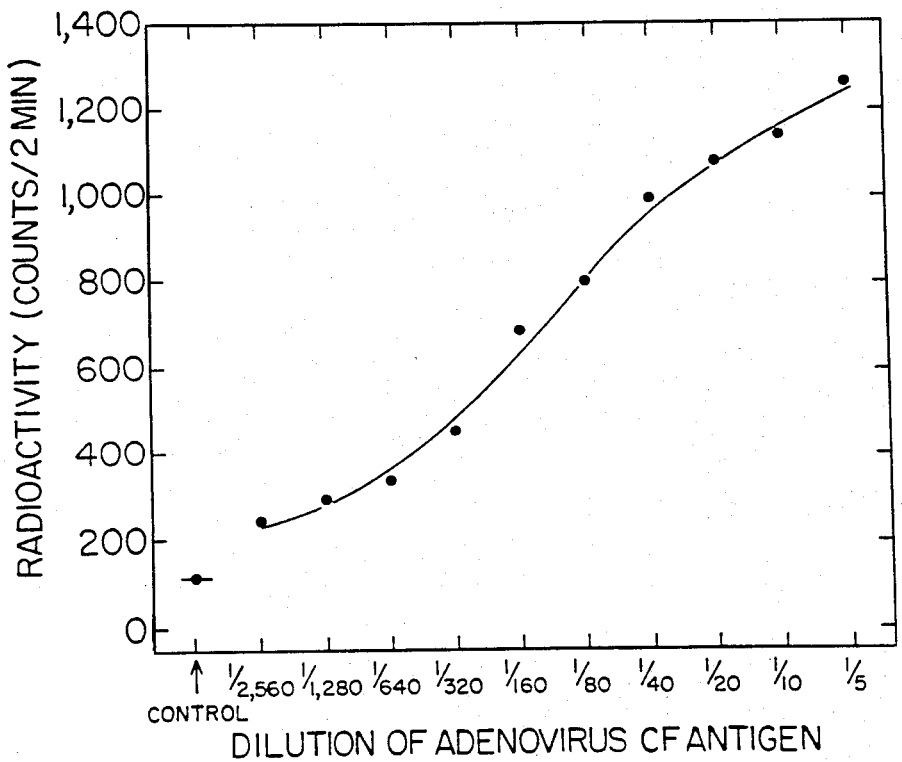
FIG. 2 shows the test results for adenovirus group-specific antigen using dinitrophenylated antibodies. Normal goat serum was used as diluent. The control corresponds to a 1:5 dilution of tissue culture medium from non-infected cells. The fluid harvested from infected cells had a CF titer of 1:32.
Figure 3:
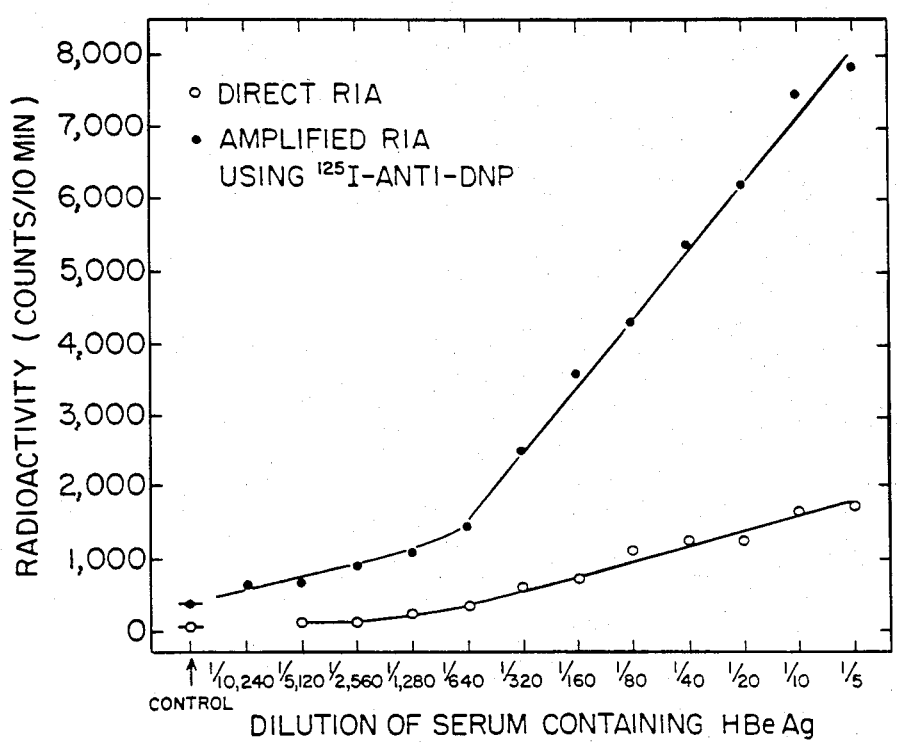
FIG. 3 shows a comparison of RIA tests for hepatitis B e-antigen (HBeAg). Dilutions of HBeAg-positive human serum in normal human serum (=control) were tested.

Results of RIA tests in which dinitrophenylated immunoglobulins were used are summarized in FIGS. 1–3. The sensitivity limit for detection of ovalbumin and ferritin was approximately 0.8 and 0.2 ng/ml, respectively (FIG. 1). This corresponds to a 4–15-fold increase in sensitivity as compared with direct RIA tests in which the corresponding immunochemically purified $^{125}$I-labeled antibodies were used. The RIA for adenovirus group-specific antigen (FIG. 2) was approximately 80× more sensitive than the CF test. Comparative RIA tests for HBeAg using either $^{125}$I-labeled IgG from anti-HBe-positive human serum or dinitrophenylated anti-HBe IgG followed by $^{125}$I-labeled anti-DNP (FIG. 3) provide evidence that haptens attached to immunoglobulins may serve as amplifiers in RIA tests. Such amplification is expected to facilitate the development of RIA tests for antigens which are inadequately characterized, difficult to purify or not available in sufficient quantities to allow the immunochemical purification of the corresponding antibodies.

The possibility of using $^{125}$I-labeled anti-DNP (or other labeled anti-hapten antibodies) as universal reagents may simplify the development of RIA tests and widen their application to various areas of research and clinical diagnosis.

What is claimed is:

1. A process for detecting the presence of an antigen in a specimen which comprises:
    (A) contacting said specimen with a substrate coated with antibodies of said antigen, incubating the so-contacted substrate and washing the substrate;
    (B) contacting the washed material of step (A) with a hapten conjugated antibody against said antigen, incubating the so-contacted material and washing the so-incubated material;
    (C) contacting the washed material of step (B) with a radioactive material labeled or enzyme containing anti-hapten antibody prepared by contacting an anti-hapten anti-serum with a haptenated antigen and recovering anti-hapten antibody from haptenated antigen and any other serum proteins, incubating the so-contacted material and washing the same; and
    (D) effecting radioimmunoassay if said anti-hapten antibody is radioactive or enzyme labeled immunoassay if said antihapten antibody is enzyme labeled, wherein said anti-hapten antibody is one prepared by contacting an anti-hapten anti-serum with a hapten containing protein, dissolving the resultant complex in a buffer which dissociates an antigen-antibody complex and separating said anti-hapten antibody from haptenated antigen.

2. A process according to claim 1, wherein said anti-hapten antibody is prepared by contacting an anti-hapten anti-serum with a hapten containing protein, dissolving the resultant pellet in a solution of urea, passing the resultant solution through a column containing a solid adsorbent and separating anti-hapten antibody from haptenated antigen.

3. A process according to claim 2, wherein said solid adsorbent is DEAE cellulose and said anti-hapten antibody is separated from haptenated antigen by elution with a solution of urea.

* * * * *